(12) United States Patent
Bilzi et al.

(10) Patent No.: US 8,153,104 B2
(45) Date of Patent: Apr. 10, 2012

(54) PHARMACEUTICAL FORMULATIONS FOR DRY POWDER INHALERS COMPRISING A LOW-DOSAGE STRENGTH ACTIVE INGREDIENT

(75) Inventors: Roberto Bilzi, Parma (IT); Angela Armanni, Parma (IT); Roberto Rastelli, Parma (IT); Daniela Cocconi, Parma (IT); Rosella Musa, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 1346 days.

(21) Appl. No.: 10/592,701

(22) PCT Filed: Mar. 16, 2005

(86) PCT No.: PCT/EP2005/002789
§ 371 (c)(1),
(2), (4) Date: May 9, 2007

(87) PCT Pub. No.: WO2005/089717
PCT Pub. Date: Sep. 29, 2005

(65) Prior Publication Data
US 2007/0202053 A1    Aug. 30, 2007

(30) Foreign Application Priority Data
Mar. 16, 2005  (EP) .................................. 04006430

(51) Int. Cl.
*A61K 9/14*   (2006.01)
*A61K 9/00*   (2006.01)

(52) U.S. Cl. .......................................... 424/46; 424/489

(58) Field of Classification Search ................... 424/46, 424/489
See application file for complete search history.

(56) References Cited

U.S. PATENT DOCUMENTS

| | | |
|---|---|---|
| 5,143,126 A | 9/1992 | Boesch et al. |
| 6,287,540 B1 | 9/2001 | Trofast |
| 6,673,335 B1 | 1/2004 | Platz et al. |
| 2002/0010318 A1 | 1/2002 | Niven et al. |
| 2003/0180227 A1 | 9/2003 | Staniforth et al. |
| 2005/0186143 A1* | 8/2005 | Stevenson et al. ............. 424/46 |
| 2009/0192187 A1* | 7/2009 | Brambilla et al. ........... 514/305 |

FOREIGN PATENT DOCUMENTS

| | | |
|---|---|---|
| EP | 1 312 357 | 5/2003 |
| WO | 95 00128 | 1/1995 |
| WO | 2005 004846 | 1/2005 |

OTHER PUBLICATIONS

U.S. Appl. No. 12/500,204, filed Jul. 9, 2009, Musa, et al.

* cited by examiner

*Primary Examiner* — James H. Alstrum-Acevedo
(74) *Attorney, Agent, or Firm* — Oblon, Spivak, McClelland, Maier & Neustadt, L.L.P.

(57) ABSTRACT

The invention provides a formulation to be administered as dry powder for inhalation suitable for efficacious delivery of low-dosage strength active ingredients to the low respiratory tract of patient. In particular, the invention provides a formulation comprising microparticles constituted of microparticles of a low-dosage strength active ingredient and microparticles of an excipient wherein the MMD of the microparticles is comprised between 2 and 15 micron, at least 10% of the microparticles has a mass diameter (MD) higher than 0.5 micron, and the process of preparation thereof.

28 Claims, No Drawings

PHARMACEUTICAL FORMULATIONS FOR DRY POWDER INHALERS COMPRISING A LOW-DOSAGE STRENGTH ACTIVE INGREDIENT

CROSS REFERENCES TO RELATED APPLICATIONS

This application is a 371 of International Patent Application No. PCT/EP05/02789, filed on Mar. 16, 2004, and claims priority to European Patent Application No. 04006430.5, filed on Mar. 17, 2004.

The present invention relates to a dry powder formulation to be administered as dry powder for inhalation suitable for efficacious delivery of low-dosage strength drugs to the low respirator tract of patients. In particular, the invention provides a dry powder formulation for inhalation freely flowable, physically and chemically stable and able of delivering both accurate doses and high respirable particle fraction of low-dosage strength active ingredients and a process of preparation thereof.

BACKGROUND OF THE INVENTION

The administration of pharmacologically active agents by inhalation is a widely used technique especially for the treatment of reversible airway obstruction, inflammation and hyperresponsiveness. The technique is also used for the administration of certain active agents having systemic action, which are absorbed via the lungs into the bloodstream.

Some of the most widely used systems for the administration of drugs to the airways are the dry powder inhalers (DPI's).

DPI's can be divided into two basic types:
i) single dose inhalers, for the administration of pre-subdivided single doses of the active compound;
ii) multidose dry powder inhalers (MDPI't) either with pre-subdivided single doses or pre-loaded with quantities of active ingredient sufficient for multiple doses each dose is created by a metering unit within the inhaler.

On the basis of the required inspiratory flow rates (1/min) which in turn are strictly depending or their design and mechanical features DPI's are also divided in:
i) low-resistance devices (>90 l/min);
ii) medium-resistance devices (about 60 l/min);
iii) high-resistance devices (about 3 l/min).

The reported flow rates refer to the pressure drop of 4 KPa (KiloPascal) in accordance with the requirements of the European Pharmacopoeia (Eur Ph) $4^{th}$ Ed 2004, page 3375.

Drugs intended for inhalation as dry powders should be used in the form of micronised powder so they are characterised by particles of few microns (μm) particle size. In powders for inhalation, the evaluation of particle size both of the active ingredient and of possible excipients or carriers is of primary importance. The particle size is quantified by measuring a characteristic equivalent sphere diameter, known as mass diameter (MD or volume diameter (VD), depending on the used technique. Particle size distribution is described by the mass median diameter (MMD) or the volume median diameter (VMD) which correspond to the diameter of 50 percent by weight or volume respectively, of the particles. The VMD is related to the MMD by the density of the particles (assuming a size independent density or the particles). In the case of active ingredients for inhalation purposes, the particle size is also expressed as mass aerodynamic diameter (MAD) and the particle size distribution as mass median aerodynamic diameter (MMAD). The MAD indicates the capability of the particles of being transported suspended in an air stream. The MMAD corresponds to the mass aerodynamic diameter of 50 percent by weight of the particles. In the prior art the term MMAD has also been improperly used for quantifying the diameter of the carrier particles The particles of active ingredient must have such a particle size as to reach the low respiratory tract. Respirable articles are generally considered to be those with MAD from 0.5 to 10 micron, as they are able of penetrating into the lower airways, i.e. the bronchiolar and alveolar sites, which are the sit of action for the pulmonary drugs and where absorption takes place for the systemic drugs. Larger particles are mostly deposited in the oropharyngeal cavity so they cannot reach said sites, whereas the smaller ones deem to be exhaled.

Hereinafter the terms drug, active ingredient, active and active substance are used as synonymous.

Although micronisation of the drug is essential for deposition into the lower respiratory tract during inhalation, it is also know that the finer are the particles, the stronger are the cohesion forces Strong cohesion forces hinder the handling of the powder during the manufacturing process (pouring, filling). Moreover they reduce the flowability of the particles while favouring in the multidose DPI's the agglomeration and the adhesion thereof to the walls. Said phenomena impair the loading of the powder from the reservoir to the metering chamber. Therefore, strong cohesion forces give rise to handling and metering accuracy problems.

Poor flowability is also detrimental to the respirable fraction of the delivered dose being the active particles unable to leave the inhaler and remaining adhered to the interior of the inhaler or leaving the inhaler as large agglomerates; agglomerated particles, in turn cannot reach the bronchiolar and alveolar sites of the lungs. The uncertainty as to the extent of agglomeration of the particles between each actuation of the inhaler and also among inhalers and different batches of particles leads to poor dose reproducibility as well.

PRIOR ART

In the prior art, for instance in WO 95/09615, one possible method of in proving the flowing properties of powders for inhalation is to agglomerate in a controlled manner, the micronised particles of a medicament to form agglomerates or pellets of relatively high density and compactness. The process includes the steps of: (i) agglomerating the micronised medicament powder by passing it through a screw feeder: and (ii) spheronizing the agglomerates preferably in a tilted rotating container. The process preferably further includes (iii) sizing the spheronized agglomerates.

Alternatively, fine articles of a micronised active ingredient have been mixed with a plurality of one or more excipients sues as lactose giving rise to a product which has been termed as soft-pellet, wherein the particles of micronised active ingredient and the particles of lactose are in an agglomerated state.

For instance WO 95/24889 discloses a powder composition comprising microfine particles of a medicament and at least one lactose pellet having a diameter of from 10 to 1500 micron which pellet comprises a plurality of microfine lactose particles.

EP 441740 claims a process and apparatus thereof for agglomerating and metering non-flowable powders preferably constituted of micronised formoterol fumarate and fine particles of lactose in order to form pellets better able to flow. In the text, it is stated that the mixing ratio of formoterol to the total mixture is within the range of from 1:10 to 1:500.

In EP 441740 it is stated that the presence of an additive such a lubricant is disadvantageous since it forms conglomerates and the conglomerations so formed are too coarse to permit sufficiently accurate metering of very small quantities.

WO 98/31351 and WO 98/31351 claim a dry powder composition comprising one or more active ingredients and a carrier substance, both of which are in finely divided form wherein the formulation has a poured bulk density of from 0.28 to 0.38 g/ml. The active substance and carrier substance are micronised, agglomerated and spheronized until the desired bulk density is obtained. The size of the agglomerates obtained is preferably in the range of from 100 to 2000 micron, more preferable from 100 to 800 micron.

However, soft pellets may reach a so high internal coherance as to compromise their breaking up into the small particles during inhalation; such drawback could be regarded as a particular critical step then medium or high-resistance multidose dry powder inhalers are used. With said inhalers, less energy is indeed available for breaking up the pellets into the small primary particles of the active ingredient.

Otherwise powders for inhalation have been formulated by mixing the micronised drug with a carrier (generally a physiologically acceptable material, commonly lactose or mannitol, preferably α-lactose monohydrate) consisting of coarser particles to give rise to "interactive ordered mixtures".

However, it is well known that the interparticle forces which occur between the active ingredient and the carrier coarse particles in the ordered mixtures may be very high so preventing the release or the micronised drug particles from the surface of the coarse ones during inhalation which is necessary for the drug particles to reach the target site into the lungs.

The surface of the coarse carrier particles is, indeed, not smooth but has asperities and clefts, which are high energy sites or which the active particles are preferably attracted to and adhere more strongly.

In order to increase the release of the active particles from the surface of the coarse carrier particles during inhalation, several approaches have been proposed.

EP 0,663,815 claims the addition of finer excipient particles (<10 micron) to coarser excipient particles (>20 micron) for controlling and optimising the amount of delivered drug during the aerosolisation phase.

Suitable excipients are monosaccharides such as glucose and arabinose, disaccharides, such as lactose, saccharose and maltose, polysaccharides, such as dextrans), polyalcohols, such as sorbitol, mannitol and xylitol, and salts such as sodium chloride and calcium carbonate.

The proportion of the active ingredient in the mixture is usually very small, eg. 0.01 to 0.1 mg of active substance to about 5 mg of excipient mixture (corresponding to from 1:50 to 1:500 ratio by weight).

The ratio between the active ingredient and the finer excipient particles is not mentioned.

WO 95/11666 describes a process for modifying the surface properties of the carrier particles by dislodging any asperities in the form of small grains without substantially changing the size of the particles in order to let the micronised drug particles to be subjected to weaker interparticle adhesion forces.

The carrier particles include any acceptable pharmacologically inert material such as crystalline sugars, preferably lactose and have a diameter comprised between 50 and 1000 micron.

The small grains have a diameter between 1 and 5 micron. Moreover, no ratios between the active ingredient particles and the small grains or between the small grains and the carrier particles are reported.

The active particles are mixed with the carrier particles. The inventors state that advantageously, the mixing is interrupted and the mixture of carrier particles and active particles is sieved to reduce the number of large agglomerates present.

'666 is silent about the presence and even more the ratio between the active ingredient and the small grains during the sieving.

WO 01/78696 ('696) claims a formulation for use in an inhaler device which comprises: i) carrier particles having a MMAD of at least 175 micron; ii) fine particles of an excipient material having a MMAD of not more than 20 micron; active particles.

The carrier particles may be of any acceptable pharmacologically inert material such as sugars as lactose.

The application '696 does not provide a general teaching about the ratios between the active ingredient and fine particles of excipient or between the active ingredient, fine excipient and/or carrier particles.

The examples refer to salbutamol sulphate, budesonide and insulin. The formulations of the examples were prepared, first by mixing the excipient fine particles and the micronised active ingredient in a 1:1 ratio by weight in a high shear mixer for 5 min then adding said mixture to the coarse fraction.

No steps of sieving are reported.

WO 01/89491 and WO 01/89492 refer to dry powder compositions comprising micronised formoterol and its combination with a micronised glucocorticosteroid, and the process of their preparation said process comprising: i) the preparation of a mixture of micronised active ingredient and micronised carrier/diluent, flowed by ii) addition of further premicronised carrier/diluent which is mixed at low energy and iii) either subjecting the mixture to agglomeration and spheronisation, or adding coarse carrier/diluent.

Preferably step iii) involves subjecting the mixture to agglomeration and spheronisation The carrier/diluent is preferably a carbohydrate, more preferably a reducing carbohydrate such as lactose glucose.

The micronized carrier/diluent has a mean particle size of less than about 25 micron, preferably less than about 10 micron, more preferably less than about 5 micron while the coarse carrier/diluent have a mean particle size of greater than about 25 micron. In the description it is specified that the mixture of the first active ingredient (formoterol) and the carrier/diluent, according to the first step can be prepared by micronising the two components together or micronising each component individually and then combining to give a micronised mixture. In the description there is no indication about a critical ratio between the active ingredient and the carrier/diluent. In the examples the micronised mixture was then subjected to agglomeration and spheronisation (i.e. to in the form of soft pellets) wherein the ratio between formoterol fumarate dihydrate and the lactose is of about 1:190, 1:7696 and 1:170000 w/w Said formulations do not contain an additive. Moreover the aim of said formulations is to obviate to the problem of the chemical stability of formoterol fumarate in the presence of a carbohydrate (e.g. lactose) and water and not to improve the dispersion of the active ingredient into the powder composition.

WO 03/024396 refers to pharmaceutical compositions, comprising: a medicament fraction, said medicament fraction comprising medicament particles having a MMAD no greater than approximately 10 micron; and at least 50% of a non-respirable excipient fraction said non-respirable excipient fraction comprising low density excipient particles having an aerodynamic diameter greater than approximately 10 micron and a geometric diameter greater than approximately 30 micron.

In an additional embodiment of the invention, the pharmaceutical compositions include a respirable excipient fraction comprising excipient particles with an aerodynamic diameter no greater than 10 micron. The preferred excipient material is mannitol.

The examples entail a step of pre-blending the coarse excipient fraction with the fine excipient or medicament fraction and subsequent blending the homogeneous first composition with a further component (i.e., medicament or fine excipient). The application is silent about the criticality of the ratio between the fine excipient and the medicament. Additives are not mentioned.

In other documents of the prior art, the use of carrier and/or excipient particles comprising an additive has been reported.

WO 96/23485 ('485) refers to a powder which includes an additive material on the surfaces of the carrier particles to promote the release of the active particles from the carrier particles on actuation of the inhaler. The additive is a material with an anti-adherent or anti-friction properties consisting of one or more compounds selected from aminoacids (preferably leucine), phospholipids, surfactants or stearates.

The trade and size of the carrier are the same of WO 95/11666. A fraction of small grains can also be present. The fraction of small grains is not characterised and the size of the grains is not specified. The application '485 is totally silent about the criticality of the ratio between the active ingredient particles and the small grains.

WO 02/43702 concerns microparticles having a MMAD of 10 micron or less for use in pharmaceutical compositions for pulmonary administration, comprising particles of an active substance having on their surfaces, particles of a hydrophobic material suitable for delaying the dissolution of the active substance. As hydrophobic material different substances can be utilised such as hydrophobic amino acid, preferably leucine, $C_{10}$-$C_{22}$ carboxylic acids and esters, amides and salts thereof preferably magnesium stearate and surface active materials as lecithin. Said compositions may comprise essentially only the microparticles or they may comprise additional ingredients such as carrier particles and flavouring agents.

WO 00/5312 refers to powders for inhalation comprising an active ingredient and carrier particles containing as additive a small amount of lubricant, 0.1-0.5% by weight, preferably magnesium stearate.

Advantageously, the carrier particles are composed on one or more crystalline sugars, preferably of α-lactose monohydrate, and have a particle size in the range 20-1000 micron, more preferably in the range 90-150 micron. The presence of carrier particles with a particle size of less than 20 micron is not contemplated.

WO 00/5315 relates to a process or obtaining a carrier for powder formulations wherein a fine faction of carrier is generated in situ. Formulations comprising an active ingredient particles, an additive and a carrier powder having a coarse fraction and a fine faction with a mean aerodynamic diameter lower than 10 μm are also envisioned.

WO 00/33789 refers to a powder or inhalable drugs comprising an active ingredient and an, recipient powder comprising a coarse first fraction (with at least 80% by weight of the particles having a particle size of at least 10 micron), a fine second fraction (with at least 90% by weight of the particles having a particle size of not more than 10 micron) and a ternary agent which is preferably a water-soluble surface-active agent with a preference for leucine. In the examples, the processes for making the powders envision the final step of mixing the carrier particles made of the coarse fraction, the fine fraction and leucine with the micronised particles of a corticosteroid.

WO 00/28979 is addressed to the use of small amounts of magnesium stearate as additive for improving the stability to the humidity of dry powder formulations for inhalation. Said formulation comprises carrier particles with a MMAD of 10-500 micron, preferably 50-200 micron and they can also contain a fraction of particles of respirable size, e.g. 0.1-10% w/w of micronised carrier. The carrier is a pharmacologically inactive substance.

In the text, it is reported that the formulations can be produced by blending the carrier material, the finely dispersed drug and magnesium stearate. The components can be added in any order. In the example 2, coarse lactose monohydrate is mixed with micronized lactose monohydrate in a tumble mixer. Following this, formoterol fumarate dihydrate and the preliminary mixture are sieved and mixed. The mixture thus obtained is mixed with magnesium stearate. The mixing conditions are not reported.

WO 01/78695 is directed to a formulation for use in an inhaler device which comprises: i) carrier particles having a MMAD of at least 175 micron; ii) active particles; and iii) additive material to the surface of the carrier particles which is able to promote release of the active particles from the carrier particles on actuation of the inhaler device. The formulation can further comprise fine particle of an excipient material of MMAD not more than 50 micron, preferably not more than 15 micron.

The carrier particles are made of any acceptable pharmacologically inert material, for example sugar alcohols and have preferably a relatively highly fissured surface. Anti-adherent agent, glidant, aminoacids, surface active materials can be used as additives.

The examples refer to salbutamol sulphate and budesonide. The formula ions are prepared, by first co-mixing or co-milling the active ingredient and the additive (leucine, magnesium stearate and others) in a ball mill, then mixing this fraction with the coarse fraction of carrier and in case with fine particles of excipient.

In WO 01/78693 the applicant has disclosed a powder for use in a dry powder inhaler the powder comprising i) a fraction or fine particles constituted of a mixture composed of particles of a physiologically acceptable excipient and magnesium stearate, the particles of said mixture having a mean particle size of less than 35 micron preferably less than 15 micron; ii) a fraction of coarse particles of a physiologically acceptable carrier having a particle size of at least 100 micron, said mixture (i) being composed of 90 to 99 percent by weight of particles of excipient and 10 to 1 percent by weight of magnesium stearate and the ratio between the fine particles and the coarse carrier particles being between 1:99 and 40:60 percent by weight; said mixture having been further mixed with one or more active ingredient in micronised form.

The carrier particles are made of any acceptable pharmacologically inert material, for example sugar alcohols.

The application is also directed to the processes for making the powder formulation: they all envision the final step of mixing the micronised particles of the active ingredient as such with the carrier particles. In WO 01/78693 application it has been demonstrated that the presence of a lubricant and in particular of magnesium stearate in the formulation improves the aerosol performance allowing a high fine particle dose of the active ingredient to be delivered to the lungs by inhalation.

All the above mentioned documents dealing with powders formulations for inhalation comprising an additive, are completely silent about the ration between the fine excipient or carrier and the active ingredient and about its criticality with respect to different embodiments for the preparation of the powder formulations.

The applicant has found that agglomerates formation may occur even when the micronised active ingredient particles are mixed with coarse excipient particles, i.e. during the dispersion of the former onto the surface of the latter ones and that the finer are the active ingredient particles, the more quickly they tend to agglomerate. In particular this phenomenon has been observed when low-dosage strength active ingredients are used with a significant amount of particles having a mass diameter lower than 1 micron, even is the presence of an additive, such as an antiadherent or lubricant which is reported to contribute to better disperd the active ingredient.

With the term low-dosage strength (also reported as low-strength for the sake of brevity) we refer to active ingredients endowed with particularly high potency which are present in the powder formulation in a very low concentration. This factor together with other properties such as high adhesiveness degree, leads to problems in the manufacturing of a composition provided with good dosage reproducibility when administered by DPI's.

The agglomeration formation is detrimental to the possibility of achieving a good uniformity of distribution of the active ingredient in the powder mixture and hence a good accuracy of the dose. The formation of agglomerates is particularly critical when a low-strength active ingredient is used. In fact, the lower is the active ingredient weight percent concentration on the total weight of the formulation, the higher is the detrimental effect of the agglomerates on the uniformity of the active ingredient in the powder blend. The unhomogeneity of the powder, due to the formation of agglomerates, involves the risk of an over or under dosage.

In view of the problem outlined above, it would be highly advantageous to provide a powder formulation, aimed at delivering low strength active ingredients by inhalation with a DPI device, which exhibits a good uniformity of distribution of the active ingredient particles and hence an adequate accuracy of the metered dose, together with a good performance in terms of delivered dose and respirable fraction.

OBJECT OF THE INVENTION

The technical problem underlying the invention is to provide a formulation to be administered as dr powder for inhalation suitable for efficacious delivery of low-dosage strength drugs to the lower respiratory tract of patients. In particular, the technical problem is to provide a formulation to be administered as dry powder for inhalation free flowable, physically and chemically stable and able of delivering both accurate doses and high respirable particle fraction of low-dosage strength active ingredients.

The offered solution is a powder formulation for use in a dry powder inhaler, the powder comprising microparticles of a low-dosage strength active ingredient and microparticles of an excipient.

According to a particular embodiment of the invention the powder formulation may further comprise particles of an additional carrier and/or particles of an additive.

Also provided is a process for the preparation of a powder formulation for efficacious delivery of low-dosage strength active ingredients said process providing a better dispersion of the active substance in the powder formulation and hence a good homogeneity, avoiding the formation of aggregates giving rise to a better uniformity of the delivered dose.

In particular there is provided a powder formulation for use in a dry powder inhaler the powder comprising microparticles composed of microparticles of a low-dosage strength active ingredient and microparticles of an excipient wherein the MMD of the microparticles is comprised between 2 and 15 micron and at least 10% of the microparticles has a mass diameter (MD) higher than 0.5 microns. Preferably, the ratio between the microparticles of active ingredient and the microparticles of excipient is between 1:60 and 1:2000, preferably 1:100 and 1:1000 by weight.

In case of very low strength active ingredients, the ratio between the active ingredient and the excipient microparticles is between 1:250 and 1:500 by weight.

DEFINITIONS

The formulation of the invention comprises a therapeutically active substance in the form, of micronised powder (the active ingredient) and non therapeutically active substances as solid diluents (the excipient and the additional carrier).

In the following description, the term "excipient" defines the non therapeutically active solid diluent present in the formulation in the form of microparticles characterized by a MMD comprised between 2 and 15 micron whereas the terms "fine carrier" and "coarse carrier" define the non therapeutically active solid diluents of the additional carrier.

DETAILED DESCRIPTION OF THE INVENTION

The characteristics of the formulation of the invention and the process of preparation thereof will be more apparent from the following detailed description.

The present invention concerns a powder formulation for use in a dry powder inhaler, the powder comprising microparticles of a low-dosage strength therapeutically active ingredient and microparticles of a non therapeutically active substance or excipient, said microparticles having a MMD comprised between 2 and 15 micron, wherein the MMD of the active ingredient is less than 10 micron preferably less than 6 micron, more preferably comprised between 1.5 and 4 micron and the MMD of the microparticles of the excipient is comprised between 2 and 15 micron and at least 10% of the microparticles has a mass diameter (MD) higher than 0.5 micron.

Advantageously the microparticles of the excipient have a MMD comprised between 2 and 15 micron preferably comprised between 2 and 10, more preferably comprised between 3 and 7 micron and, in certain cases in particular when a very low-strength active ingredient whose nominal dose is equal to or lower than 4 μg is used, the MD of the 90% of the microparticles is advantageously equal to or lower than 60 micron preferably equal to or lower than 50 micron, more preferably equal to or lower than 30 micron. In a preferred embodiment, the MD of the microparticles of the excipient is comprised between 1 and 20 micron, preferably between 1 and 15 micron and the MMD is comprised between 3 and 7 micron.

The ratio between the microparticles of the active ingredient and the microparticles of the excipient is comprised between 1:1 and 1:2000 by weight, preferably between 1:15 and 1:1000, more preferably between 1:20 and 1:500. According to a preferred embodiment the ratio is comprised between 1:60 and 1:2000, preferably 1:100 and 1:1000 by weight.

In case of very low strength active ingredients the ratio between the active ingredient and the excipient microparticles is between 1:250 and 1:00 by weight.

For the purposes of the invention, low-dosage strength active agents are those active ingredients whose nominal dose delivered after each actuation of the inhaler is equal to or lower than 20 μg, or 12 μg, or 10 μg, or 8 μg, or 6 μg, or 5 μg, or 4 μg, or 3 μg.

Nominal doses of active ingredient even of from 0.5 or 3.0 μg can be helpfully delivered in the formulation of the invention.

The excipient particles may be constituted of any amorphous or crystalline physiologically acceptable non therapeutically active material of animal or vegetal source or combination thereof; preferred materials are crystalline sugars and for example monosaccharides such as glucose or arabinose, or disaccharides such as maltose, saccharose, dextrose or lactose. Polyalcohols such as mannitol, sorbitol, maltitol, lactitol can also be used.

The preferred material is lactose and more preferably is α-lactose monohydrate.

Examples of commercial α-lactose monohydrate are Capsulac® and Pharmatose®. An example of commercial mannitol is Pearlitol®.

Depending on the characteristics of the active ingredient and its percent amount in the formulation and the kind of dry powder inhaler used for its administration the powder formulation of the invention may comprise essentially only microparticles of the active ingredient and of the excipient or it may comprise additional carrier particles and/or an additive.

It has been indeed found that, in certain cases, if the micronised particles of the active ingredient, before they are diluted with additional carrier particles are mixed with micronised excipient particles in the proposed weight ratio, a better dispersion of the active substance in the powder formulation can be achieved and hence a good homogeneity, avoiding the formation of aggregates. A good homogeneity in turn gives rise to a better uniformity of the delivered dose, especially when the active ingredient is present in a low-dosage strength.

The homogeneous dispersion of the active ingredient in the powder, and the absence of aggregates of active particles can be established using a Near Infrared spectrophotometer equipped with a microscopy imaging system (Near Imaging).

In a preferred embodiment of the invention, and in particular when the formulation is delivered by a multiple dose DPI, microparticles consisting of particles of a low-dosage strength active ingredient and microparticles of an excipient are diluted with particles of an additional non therapeutically active carrier.

The particles of the additional carrier may comprise ire particles, coarse particles and a mixture thereof.

Advantageously the additional carrier particles further comprise one or more additives to promote the release of the active particles from the excipient and the carrier particles on actuation of the inhaler. The preferred additive is an anti-adherent material or a lubricant.

The fine and coarse particles of the additional carrier may be constituted of any amorphous or crystalline physiologically acceptable non therapeutically active material of animal or vegetal source or combination thereof. Preferred materials are crystalline sugars and for example monosaccharides such as glucose or arabinose, or disaccharides such as maltose, saccharose, dextrose or lactose. Polyalcohols such as mannitol, sorbitol, maltitol, lactitol can also be used.

The preferred material is lactose and more preferably is α-lactose monohydrate.

Preferably, the excipient and the coarse and fine carrier particles constituted of the same physiologically acceptable non therapeutically active material.

In a particular embodiment of the invention, the additional carrier consists of:
 i) a fraction of fine particles constituted of a mixture composed of fine carrier particles and particles of an additive with anti-adherent or lubricant properties (the fine carrier fraction);
 ii) a fraction of coarse carrier particles (the coarse carrier fraction).

The formulation of the present invention shows either excellent rheological properties and physical and chemical stability without subjecting the powder to conditioning treatments such as that envisioned in WO 01/89491 and WO 01/89492. It also exhibits a good aerosol performance.

Moreover, in said formulation the active ingredient is homogeneously distributed.

Generally, the fine carrier particles have a MMD of less than 50 micron, preferably less than 35 micron, more preferably comprised between 3 and 15 micron with a MD comprised between 1 and 100 micron, preferably between 1 and 70 micron.

Advantageously the MMD of the coarse carrier particles is higher than 90 micron. Preferably the coarse particles have a MD comprised between 50 micron and 500 micron, more preferably between 150 and 400 micron, even more preferably between 210 and 355 micron.

The coarse carrier particles may have a relatively highly fissured surface, that is, on which there are lefts and valleys and other recessed regions referred to herein collectively as fissures.

The "relatively highly fissured" coarse carrier particles can be defined in terms of fissure index or rugosity coefficients as disclosed in WO 01/78695 and WO 01/78693 and the can be characterised according to the description therein reported.

The fissure index is advantageously not less than 1.5, while the rugosity coefficient is at least 1.25.

Said coarse carrier particles can also be characterised in terms of tapped density or total intrusion volume measured as reported in WO 01/78695.

The tapped density of the oars carrier particles is advantageously less than 0.8 g/cm$^3$, preferably between 0.8 and 0.5 g/cm$^3$.

The total intrusion volume is of at least 0.8 cm$^3$ preferably at least 0.9 cm$^3$.

The additive may include a combination of one or more materials. Advantageously the additive is a material with anti-adherent properties such as the aminoacids leucine and isoleucine. The additive may also consist of one or more water-soluble surface active materials, for example lecithin, in particular soya lecithin.

Preferably the additive is a water-insoluble lubricant such as magnesium stearate; sodium stearyl fumarate; sodium lauryl sulphate, stearyl alcohol, stearic acid and sucrose monopalmitate. In a more preferred embodiment of the invention, the additive is magnesium stearate, and its particles at least partially form a continuous envelop around the surface of the excipient particles.

Advantageously, the MMD of the additive is less than 50 micron, preferably less than 35 micron, more preferably less than 15 micron.

Advantageously, the amount of additive in the final formulation is comprised between 0.02 and 4.0 percent by weight (which equates to 4 g per 100 g of the final formulation), preferably between 0.05 and 2.0 percent by weight on the total weight of the formulation.

In the case of magnesium stearate, the amount is comprised between 0.02 and 1.0 percent by weight, preferably between 0.05 and 0.5 percent by weight, more preferably between 0.1 and 0.4 percent by weight on the total weight of the formulation.

The invention also provides a process for preparing the formulation.

In a particular embodiment the process involves the preparation of microparticles consisting of microparticles of the active ingredient and microparticles of a physiologically acceptable excipient.

Said microparticles can be prepared by mixing and then micronising the two components together by milling. Alternatively, each component can be micronised individually and then combined by mixing.

In a first embodiment, the microparticles are prepared by mixing, then micronising the two components together in a mortar or in a mill.

As a first step, the particles of the active ingredient and the particles of the excipient are mixed together in a conventional mixer such as Turbula mixer operating at a speed comprised between 8 and 72 r.p.m., preferably between 16 and 32 r.p.m. for at least one hour, preferably at least two hours, more preferably up to five hours, then co-micronised in a mill.

A wide range of milling devices, such as ball mill, hammer mill or knife mill, and operating conditions thereof, are suitable for preparing the microparticles of the invention.

Preferably, the particles are co-micronised by using a jet mill by suitably modulating the relevant parameters.

It has indeed been found that by suitably modulating the pressure and other parameters such as the feeding rate at which the jet mill operates it is possible to control the micronisation process in such a way as to increase the yield of the process as well as to achieve the desired particle size distribution. Said particle size is optimal for avoiding the formation of stable agglomerates when the microparticles are mixed with additional carrier particles.

For example, when a Glove Box 100 W jet mill is used, microparticles fulfilling the requirements of the invention are obtained by using a grinding pressure of 7 bar and a feeding rate of 1.5-2.0 kg/h.

Advantageously, the starting MD of the excipient particles, before co-micronisation, is comprised between 20 and 1000 micron, preferably between 50 and 400 micron, more preferably between 212 and 355 micron.

The active ingredient particles may also be in a micronised form before they are co-milled with the excipient particles.

Alternatively, microparticles consisting of micronised particles of the active ingredient and micronised particles of a physiologically acceptable excipient can be prepared by micronising each component individually and then combining them by mixing in a conventional manner, and for example as described before or page 20, lines 19-23.

In the embodiment of the process of the invention the microparticles have a starting MMD comprised between 2 and 15 micron, preferably comprised between 2 and 10 micron, more preferably comprised between 3 and micron. The MD of the microparticles is comprised between 1 and 20 micron, preferably between 1 and 15 micron and at least 10% of the microparticles has a MD higher than 0.5 micron.

In the above described embodiments, for the preparation of the microparticles, the ratio between the microparticles of the active ingredient and the microparticles of the excipient is between 1:5 and 1:100 by weight, preferably between 1.9 and 1.90, more preferably between 1:15 and 1:80, more preferably between 1:20 and 1:75 even more preferably between 1:20 and 1:60.

The process can further include the step of the addition by mixing of the microparticles to additional carrier particles as defined above.

The particles of the additional carrier may comprise fire particles, coarse particles and a mixture thereof. Advantageously the additional carrier particles further comprise one or more additives to promote the release of the active particles from the excipient and the carrier particles on actuation of the inhaler. The preferred additive is an anti-adherent material or a lubricant.

The process of mixing can be carried out according to methods disclosed in the prior art and well known to the person skilled in the art, and for example as reported before on page 20, lines 19-23.

The additional carrier particles comprising fine carrier particles, coarse carrier particles, optionally additive particles and their mixtures, can be prepared by co-mixing together the fine carrier, the coarse carrier and optionally the additive particles, in any order and combination, for at least two hours.

When the additional carrier particles comprise fine and coarse carrier particles, the ratio between the fine carrier particles and the coarse carrier particles is comprised between 1:99 and 40:60 percent by weight, preferably between 5:95 and 30:70 percent by weight, even more preferably between 10:90 and 20:80 percent by weight.

Advantageously the fine and/or coarse additional carrier particles include from 0.02 to 10 percent by weight of additive particles on the weight of the final formulation, preferably from 0.05 to 5% w/w, more preferably form 0.1 to 1 percent by weight on the total weight of the final formulation.

In a further embodiment the additional carrier comprises a fine carrier fraction, and a coarse carrier fraction as defined on page 18, lines 10-15. The fine carrier fraction can be prepared according to the methods described in the patent application WO 01/78693, whose teaching is incorporated in full in the present application.

The fine carrier particles and the additive particles are co-micronised it order to reduce their particle size to a MMAD of less than 35 micron and optionally making the additive particles fall or partially, continuously or discontinuously coating the surface of the excipient particles. The resulting mixture is then mixed with the coarse carrier particles such that fine carrier fraction particles adhere to the surface of the coarse carrier particles.

Alternatively, the fine carrier fraction can be prepared by mixing in a high-energy mixer the fine carrier particles and the additive particles having a MMD of less than 35 micron.

In a preferred embodiment of the invention, the additional carrier particles consist of a fine carrier fraction and a coarse carrier fraction as define above, wherein the fine carrier fraction is composed from 90 to 99 percent by weight of $\alpha$-lactose monohydrate particles and from 10 to 1 percent by weight of magnesium stearate particles, preferably 98 to 2, and the ratio between the fine carrier fraction and the coarse carrier fraction made of $\alpha$-lactose monohydrate particles is from 15 to 85 to 5:95, preferably 10 to 90 percent by weight.

Advantageously, the magnesium stearate particles coat, at least partially, the surface of either the tin or the coarse carrier particles.

Advantageously the formulation of the invention has an apparent density before settling of at least 0.5 g/ml, preferably from 0.6 to 0.7 g/ml and a Carr index of less than 25, preferably less than 15.

The formulation of the invention can be in the form of "hard pellets", obtained by subjecting the mixture to a spheronisation process.

By the term of "hard pellets" we mean spherical or semi-spherical units whose core is made of coarse carrier particles that easily de-aggregate when delivered.

By the term "spheronisation" we mean the process of "rounding off" of the particles which occurs during the treatment.

The spheronisation step will be carried out by mixing the coarse carrier fraction and the fine carrier fraction in a suitable mixer, e.g. tumbler mixers such as Turbula, rotary mixers or high-energy mixers such as Diosna for at least 5 minutes, preferably for at least 30 minutes, more preferably for a least two hours, even more preferably for four hours. In a general way, the person skilled in the art will adjust the time of mixing and the speed of rotation of the mixer to obtain homogenous mixture.

The ratio between the microparticles and the additional carrier particles will depend on the type of inhaler device used and the required dose of the active ingredient. Advantageously the ratio be wen the microparticles and the additional carrier particle is between 5:95 and 0.1:99, preferably 10:90 and 0.25:99.75 by weight, more preferably between 2:98 and 0.5:99.5 by weight.

The microparticles are mixed with the carrier particles in a suitable mixer, preferably in a Turbula mixer for at least 30 min, preferably for one hour, preferably for two hours, more preferably for at least three hours, operating at a speed comprised between 8 and 72 r.p.m., preferably at 16 or 32 r.p.m.

After the mixing the content uniformity of the active ingredient, expressed as relative standard deviation (RSD), is less than 6%, preferably less than 5%, more preferably equal/less than 2.5%, even more preferably equal or less than 1.5%.

In certain cases, and in particular in the presence of a very low strength active ingredient, when the homogeneity of the powder and the absence of aggregates is particularly critical to assure uniformity of the doses, the formulation of the invention is prepared according to the following process.

The active ingredient particles in a micronised form and a non therapeutically active solid diluent consisting of micronised particles of a physiologically acceptable excipient, helpfully a portion of additional carrier comprising fine carrier particles and or coarse carrier particles and optionally additive particles, are forced through a sieve in order to facilitate the dispersion of the active ingredient and avoid the formation of agglomerates.

Advantageously, in this particular embodiment, the ratio between the active ingredient particles and the excipient particles is comprised between 1:1 and 1:3 by weight, preferably between 1:1.5 and 1:2, and the ratio between the active ingredient particles and the non therapeutically active solid diluent consisting of the excipient particles and the additional carrier particles is comprised between 1:10 and 1:100 by weight, preferably between 1:10 and 1:50, more preferably between 1:20 and 1:30 by weight.

The preferred additive is a lubricant, more preferably magnesium stearate.

Advantageously the sieve mesh size is comprised between 100 and 400 micron, preferably between 200 and 300 micron, and more preferably is of 250 micron.

In a preferred embodiment said process is carried out by using micronised active ingredient particles, micronised excipient particles, coarse carrier particles, and magnesium stearate as additive in such a way that at the ratio between the active ingredient and the excipient particles is between 1:1.5 and 1:2 by weight and the ratio between the active ingredient and excipient, coarse carrier particles and magnesium stearate is between 1:10 and 1:20 by weight.

In a more preferred embodiment, the micronised excipient particles, magnesium stearate and the coarse carrier particles are pre-mixed in a ratio comprised between 14.7:0.3:85 and 5:02:94.8 by weight, preferably 9.8:0.2:90 by weight, before adding the active ingredient microparticles and forcing the mixture through the sieve.

In said embodiment, the excipient and the coarse carrier consist of α-lactose monohydrate and the MMD of the excipient is comprised between 2 μm and 15 μm.

The process further includes the step of the addition by mixing of the mixture resulting from the process of sieving to the additional carrier in such a way that the percentage of the active ingredient in the final formulation is comprised between 0.005 and 0.05% on the total weight of the final formulation. The process of mixing can be carried out as reported on page 20, lines 19-23.

The active ingredient particles referred to throughout the specification will comprise an effective amount of at least one low-dosage strength active substance that can be delivered to the lungs in form of a powder for inhalation by means of a DPI. The substance may act either locally, at pulmonary level, or, after passage in the bloodstream, at systemic level.

The active ingredient particles advantageously consist essentially of one or more therapeutically active agents.

References herein to any active agent are to be understood to include any physiologically acceptable derivative. In the case of the $β_2$-agonists, physiologically acceptable derivatives include salts, solvates and solvates of salts.

Suitable therapeutically active agents include drugs which are usually administered orally by inhalation for the treatment of respiratory diseases. Examples of high potent respiratory drugs are the long-acting $β_2$-agonists such as 8-hydroxy-5-[(1R)-1-hydroxy-2-[[(1R)-2-(4-methoxyphenyl)-1-methylethyl]amino]ethyl-2(1H)-quinolinone, and its salts.

Suitable salts, for the purposes of the invention, include hydrochloride, phosphate, salicylate and mandelate salts.

The preferred salt is the hydrochloride salt, sometimes also referred to as TA 2005 and reported in the following with the experimental code CHF 4226.

Otherwise the active ingredient can be selected from low-dosage strength active substance for systemic use, for example peptides or a polypeptides such as cyclosporin, insulin, human growth hormone, calcitonin and erythropoietin, or decoy or antisense oligonucleotides.

The active particles preferably comprise CHF 4226.

Advantageously, the nominal dose of CHP 4226 is in the range of 0.5 to 8 μg, preferably of 1 to 4 μg, more preferably 1 to 2 μg or 0 to 4 μg.

A particular realization of the invention concerns 8-hydroxy-5-[(1R)-1-hydroxy-2-[[(1R)-2-(4-methoxyphenyl)-1-methylethyl]amino]ethyl-2(1H)-quinolinone hydrochloride or CHF 4226 in a powder formulation comprising microparticles of excipient and, optionally, fine and/or coarse additional carrier particles and/or an additive, according to the definitions of the present application, wherein CHF 4226 is present in an amount between 0.005% and 0.05% on the total weight of the final formulation.

In a more particular realization of the invention, the formulation comprises microparticles of CHF 4226 in a amount comprised between 0.005 and 0.05%, microparticles of excipient made of α-lactose monohydrate with a MMD comprised between 2 and 15 micron, coarse carrier particles made of a-lactose monohydrate with a MD comprised between 212 and 355 micron, and magnesium stearate and is prepared according to the process disclosed from page 25 line 23 to page 26 line 13.

If desired, the active particles may comprise CHF 4226 in combination with additional active ingredients selected from the group of corticosteroids such as budesonide and its epimers, beclometasone dipropionate, triamcinolone acetonide, fluticasone propionate, flunisolide, mometasone furoate, rofleponide and ciclesonide; the group of anticholinergic or antimuscarinic agents such as ipratropium bromide, oxytropium bromide, tiotropium bromide, glycopyrrolate bromide or revatropate and their enantiomers; the group of phosphodiesterase-4 (PDE-4) inhibitors such as cilomilast and roflumilast, and their combinations, provided that they are compatible with one another under conditions of storage and use.

When present, the additional active ingredients are added to the first active ingredient and/or to the excipient particles, optionally in presence of additional carrier particles, then co-mixed and optionally co-sieved or co-mixed and co-milled according to the teaching reported above to form the microparticles.

The formulation of the invention is particularly suitable for delivering low-dosage strength active ingredients by using a high- or medium resistance DPI device.

The formulation may also comprise additional components such as flavouring agents.

The invention is illustrated by the following examples.

In view of the disclosure in the present application, the person skilled in the art will be able to reproduce the teaching herein provided by using other kinds of excipients or additional carrier and their mixture.

Example 1

Preparation of Microparticles Containing CHF 4226 Hydrochloride as Active Ingredient and Different Types of α-Lactose Monohydrate by Co-Milling at Different Pressures Micronised CHF 4226 hydrochloride and different types of α-lactose monohydrate in different ratios by weight were mixed in a Turbula mixer for a suitable mixing time at 32 r.p.m, then co-milled in a jet mill apparatus at different operating conditions in order to obtain different particle size distribution.

The microparticles were characterised in terms of uniformity of distribution of the active ingredient, particle size and apparent densities.

The particle size of the obtained microparticles was determined by laser diffraction analysis. The parameters taken into consideration were: i) the VD in micron of 10%, 50%, and 90% of the particles expressed as d(v, 0.1), d(v, 0.5) and d(v, 0.9), respectively, which correspond to the mass diameter assuming a size independent density for the particles. ii) the polydispersity of the powder, i.e. the width of the particle size distribution which is expressed by the span (span=[d(v, 0.9)− d(v, 0.1)]/d (v, 0.5)—according to Chew N Y et al *J Pharm Pharmaceut Sci* 2002, 5, 162-168).

The apparent densities were calculated according to the method reported as follows.

Powder mixtures (100 g) were poured into a glass graduated cylinder and the unsettled apparent volume $V_0$ was read; the apparent density before setting (poured density, dv) was calculated dividing the weight of the sample by the volume $V_0$. After 1250 taps with the described apparatus, the apparent volume after settling ($V_{1250}$) was read and the apparent density after settling (tapped density, ds) was calculated.

The relevant data are reported in Table 1.

TABLE 1

Particle size distribution of the different compositions

| | Batch 1 | Batch 2 | Batch 3 | Batch 4 |
|---|---|---|---|---|
| Ratio between the active ingredient and the excipient (w/w) | 1:24 | 1:24 | 1:49 | 1:49 |
| Type of lactose | Capsulac ® | Capsulac ® | Capsulac ® | Spherolac ® 100 |
| Starting particle size (μm) | 212-355 | 212-355 | 212-355 | 50-400 |
| Final particle size (μm) | | | | |
| d (v, 0.1) | 1.06 | 0.69 | 1.10 | 1.07 |
| d (v, 0.5) | 2.79 | 1.66 | 2.79 | 2.64 |
| d (v, 0.9) | 6.03 | 3.05 | 5.66 | 5.21 |
| Span | 1.78 | 1.42 | 1.63 | 1.57 |
| Apparent density (g/ml) | | | | |
| poured density (ds) | — | — | 0.75 | — |
| tapped density (ds) | — | — | 1.04 | — |

All the preparations showed a good uniformity of distribution of the active ingredient as they exhibited a RSD lower than 6%.

As it can be appreciated from Table 1, different particle size distribution of the microparticles were obtained, varying the feed rate at which the jet mill apparatus operated. All the microparticle fractions have at least 10% of the particles with a MD higher than 0.5 micron and MMD higher than 2 micron except for the Batch 2. The various batches of microparticles were then added to a carrier made of coarser particles. Batches 1, 3 and 4 uniformly dispersed into the carrier and after a suitable time of mixing no agglomerates were observed. In the formulation prepared starting from batch 2 constituted of microparticles having a MMD lower than 2 micron, agglomerates where still present after longer period i.e. ten hours of mixing.

The agglomerates were isolated by sieving and their particle size distribution determined by laser diffraction analysis.

The results are reported in Table 2 for comparison with the particle size distribution of the microparticles of batch 2.

TABLE 2

Particle size distribution of the agglomerates

| Particle size (μm) | Agglomerates (10 min) | Batch 2 |
|---|---|---|
| d (v, 0.1) | 0.49 | 0.69 |
| d (v, 0.5) | 1.38 | 1.66 |
| d (v, 0.9) | 2.85 | 3.05 |
| Span | 1.71 | 1.42 |

From the analysis, it appears that the agglomerates are formed by the finer particles of the microparticle fraction composed by the excipient and the active ingredient.

It follows that fractions having the d(v, 0.1) and d(v, 0.5) of the particles moved towards finer size, i.e. equal or less than 0.5 micro and less than 2 micron, respectively, give rise to stable agglomerates which cannot be dispersed even after long time of mixing (more than 10 hours). This is detrimental to the uniformity of distribution of the active ingredient in the final formulation.

Example 2

Preparation of Microparticles Constituted of CHF 4226 Hydrochloride and Different Types of α-Lactose Monohydrate by Co-Mixing Micronised CHF 4226 hydrochloride having a MMD of 1.8 micron and micronised α-lactose monohydrate having a MMD of about 12.5 micron in a ratios 1:2, 1:9, 1:24 and 1:99 percent by weight were mixed in mortar to obtain different batches of microparticles.

The microparticles were characterised in terms of particle size (laser diffraction analysis) and uniformity of distribution of the active ingredient.

The results are reported in Table 3.

TABLE 3

Technological parameters of the microparticles

|  | Batch 1 | Batch 2 | Batch 3 | Batch 4 |
|---|---|---|---|---|
| Ratio | 1:2 | 1:9 | 1:24 | 1:99 |
| Particle size distribution (μm) | | | | |
| d (v, 0.1) | 0.56 | 1.02 | 1.53 | 2.50 |
| d (v, 0.5) | 2.09 | 5.19 | 9.92 | 12.92 |
| d (v, 0.9) | 23.93 | 29.2 | 54.32 | 51.70 |

All the batches of microparticles showed a good uniformity of distribution of the active ingredient as they exhibited a RSD lower than 6% and, in all cases at least 10% of the particles had a MD higher than 0.5 micron with a MMD higher than 2 micron and equal or lower than 15 micron.

The various batches of microparticles were then added to a carrier made of coarse particles. Batches 2, 3 and 4 uniformly dispersed in the final formulation. In this kind of preparation we can observe that Batch 1, wherein the ratio between the active ingredient and the excipient was 1:2, did not exhibit a good uniformity of distribution of the active ingredient and the RSD was of 13.2%.

Example 3

Preparation of a Formulation Consisting of Microparticles Made of Co-Micronised CHF 4226 Hydrochloride and α-Lactose Monohydrate in the Ratio 1:49 w/w, and a Carrier Comprising a Fine Carrier Fraction and a Coarse Carrier Fraction a) Preparation of the fine carrier fraction.
  α-lactose monohydrate SpheroLac® 100 with a starting of 50 to 400 micron (MMD of about 170 micron) and magnesium stearate with a starting MD of 3 to 35 micron (MMD of about 10 micron) in the ratio 98:2 percent by weight were co-milled in a jet mill apparatus.
b) Addition of the fine carrier fraction to the coarse carrier fraction.
  89.5 percent by weight of α-lactose monohydrate CapsuLac® (212-355 micron) was placed in a 240 ml stainless steel container, then 10 percent by weight of the fine carrier fraction was added.
  The blend was mixed in a lab Turbula mixer for 4 hours at 32 r.p.m. to obtain the carrier.
c) Addition of the microparticles fraction to the carrier.
  Micronised CHF 4226 hydrochloride and α-lactose monohydrate Capsulac® (212-355 micron) in the ratio of 1:49 percent of Batch 3 of example 1 were added to the carrier in a suitable amount in order to obtain a ratio of 1 μg of active ingredient to 10 mg of final formulation and mixed in a Turbula mixer for three hours at 32 r.p.m. The amount of magnesium stearate in the final formulation was 0.2 percent by weight.

Example 4

Technological Characterisation of the Formulation of Example 3

The formulation of Example 3 was characterised by its density/flowability parameters and uniformity of distribution of the active ingredient.

The apparent densities were calculated as reported in the Example 1.

The flowability properties were tested according to the method reported below.

Powder mixtures (about 110 g) were poured into a dry funnel quipped with an orifice of suitable diameter that is blocked by suitable mean. The bottom opening of the funnel is unblocked and the time needed for the entire sample to flow out of the funnel recorded. The flowability is expressed in seconds and tenths of seconds related to 100 g of sample.

The flowability was also evaluated from the Carr's index calculated according to the following formula:

$$\text{Carr's index } (\%) = \frac{ds - dv}{ds} \times 100$$

A Carr index of less than 25 is usually considered indicative of good flowability characteristics.

The uniformity of distribution of the active ingredient was evaluated by withdrawing 10 samples, each equivalent to about a single dose, from different parts of the blend.

The results are reported in Table 4.

TABLE 4

Technological Parameters of the formulation

| Apparent density | |
|---|---|
| poured density ($d_v$) | 0.68 g/ml |
| tapped density ($d_s$) | 0.77 g/ml |
| Flowability | |
| Flow rate through 4 mm Ø | 140.6 s/100 g |
| Carr Index | 11.7 |
| Uniformity of distribution of active ingredient | |
| RSD | 2.5% |

The formulation of the invention shows a good uniformity of distribution of the active ingredient as demonstrated by the low RSD. It also exhibits very good flow properties as demonstrated by the Carr index; this parameter is very important to obtain consistency of the metered dose when a multi-dose dry powder inhalers with powder reservoir is used.

Example 5

Determination of the Aerosol Performances of the Formulation of Example 3

An amount of powder for inhalation was loaded in a multidose dry powder inhaler.

The evaluation of the aerosol performance was effected using the Multi Stage Liquid Impinger (MSLI) apparatus (Apparatus C) according to the conditions reported in the Eur Ph 4$^{th}$ Ed 2004, par 2.9.18, pages 213-219 After aerosolization of 10 doses, the MSLI apparatus was disassembled and the amounts of drug deposited in the stages were recovered by washing with a solvent mixture and then quantified by High-Performance Liquid Chromatography (HPLC). The following parameters were calculated: i) the delivered dose which is the amount of drug delivered from the device recovered in the impactor; ii) the fine particle dose (FPD) which is the amount of delivered dose recovered below 5 microns; iii) the fine particle fraction (FPF) which is the percentage of the fine particle dose relative to the delivered dose reaching the stage 2 of MSLI; iv) the MMAD.

The results in terms of aerosol performance are reported in Table 5.

TABLE 5

| Aerosol performance | | | |
|---|---|---|---|
| Delivered dose µg | FPD µg | FPF % | MMAD µm |
| 0.82 | 0.44 | 53.9 | 1.53 |

The aerosol performances of the formulation are very good with more than 50% of FPF.

Example 6

Formulation Consisting of Microparticles Made of CHF 422 Hydrochloride and α-Lactose Monohydrate in Different Ratios w/w Obtained by Co-Mixing Pre-Micronised Particles, and a Carrier Comprising a Fine Carrier Fraction and a Coarse Carrier Fraction a) Preparation of the formulations The carrier was prepared as described in the Example 3.

The microparticles were prepared as described in the Example 2.

The microparticles were added to the carrier in a suitable amount in order to obtain a ratio of 1 µg of active ingredient to 10 mg of final formulation and mixed in a Turbula mixer for one hour at 32 r.p.m.

b) Technological characterisation of the final formulations

The final formulations were characterised by their density/flowability parameters and uniformity of distribution of the active ingredient as reported in the Example 4.

The results are reported in Table 6.

TABLE 6

| Technological Parameters of the final formulation | | | |
|---|---|---|---|
| | Ratio | | |
| | 1:9 | 1:24 | 1:99 |
| Apparent density | | | |
| Poured density ($d_v$) -g/ml- | 0.67 | 0.66 | 0.67 |
| Tapped. density ($d_s$) -g/ml- | 0.74 | 0.74 | 0.74 |
| Flowability | | | |
| Flow rate through 4 mm Ø -s/100 | 136.4 | 145.2 | 141.2 |
| Carr Index | 9.5 | 10.8 | 9.5 | c) Determination of the aerosol performance of the final formulations.

The aerosol performances were determined as reported in the Example 5.

The results are reported in Table 7.

TABLE 7

| Aerosol performances | | | | |
|---|---|---|---|---|
| Ratio | Delivered dose µg | FPD µg | FPF % | MMAD µm |
| 1:9 | 1.00 | 0.46 | 47.1 | 1.72 |
| 1.24 | 0.82 | 0.44 | 53.9 | 1.53 |
| 1:99 | 1.00 | 0.54 | 53.3 | 1.42 |

All the formulations show excellent characteristics in terms of either uniformity of distribution of the active ingredient (RSD lower than 5%) and aerosol performances.

In the case of the ratio 1:24 and 1:99 a FPF higher than 50% has been achieved.

Example 7

Preparation of a Formulation Comprising Microparticles of CHF 4226, Microparticles of Excipient, Coarse Carrier Particles and Magnesium Stearate a) Preparation of a non therapeutically active solid diluent consisting of a mixture of microparticles of excipient coarse carrier particles and magnesium stearate.

Particles of α-lactose monohydrate with a MD comprised between 1 and 15 micron and a MMD comprised between 3 and micron, were mixed with magnesium stearate and coarse carrier particles of α-lactose monohydrate with a MD comprised between 212 and 355 micron in the ratio 9.8:0.2:90 by weight, respectively.

b) To about 60 g of the mixture a) 3.2 g of micronized CHF4226 were added in such a way that the ratio between the active ingredient and the non therapeutically active solid diluent was of about 1:20 by weight and the resulting mixture was sieved through 250 µm mesh.

c) The mixture obtained in step b) was then added to the remaining solid diluent mixture a) to have an amount of 4 µg of active ingredient in 10 mg of the final formulation (0.04%) and mixed in an industrial Turbula mixer for 1 hour at 16 r.p.m. The amount of magnesium stearate in the final formulation was 0.2 percent by weight.

The formulation was characterised by its density-flowability parameters, uniformity of distribution of the active ingredient and aerosol performances.

The apparent densities were calculated as reported in the Example 1.

The flowability properties and the uniformity of distribution were determined as reported in the Example 4.

The evaluation of the aerosol performance was carried out by means of an Andersen Cascade Impactor according to the conditions reported in the *Eur Ph 3$^{rd}$ Ed Suppl.* 2001, par 2.9.18 pages 123-124, determining the same parameters reported in the Example 5.

The results are reported in Tables 8 and 9.

TABLE 8

Technological Parameters of the formulation

| Apparent density | |
|---|---|
| poured density ($d_v$) | 0.68 g/ml |
| tapped density ($d_s$) | 0.77 g/ml |
| Flowability | |
| Flow rate through 4 mm Ø | 110.8 s/100 g |
| Uniformity of distribution of active ingredient | |
| RSD | 1.0% |

TABLE 9

Aerosol performance of the formulation

| Delivered dose µg | FPD µg | FPF % | MMAD µm |
|---|---|---|---|
| 3.0 | 1.9 | 63.7 | 2.0 |

As it can be appreciated, the formulation of the invention shows a good uniformity of distribution of the active ingredient as demonstrated by the low RSD as well as very good flow properties as demonstrated by the flow rate. Also the aerosol performances of the formulation are very good with more than 60% of FPF.

Moreover, the active ingredient in the formulation turned out to be physically and chemically stable after storage for three months in a warehouse under controlled environmental conditions as demonstrated by the assay of CHF 4226 that remained substantially unchanged and the aerosol performance after the storage wherein the delivered dose was of 3.0 µg and remained unchanged.

Moreover no degradation products were detected.

The invention claimed is:

1. A powder formulation for use in a dry powder inhaler, said powder comprising:
   (a) microparticles of a low-dosage strength active ingredient for the treatment of respiratory diseases having a therapeutical nominal dose equal to or lower than 4 microgram on each actuation of a powder inhaler; and
   (b) microparticles of an excipient selected from the group consisting of glucose, arabinose, maltose, saccharose, dextrose, and lactose,
   wherein:
   both microparticles (a) and microparticles (b) have a d(0.1) higher than 0.5 microns and a d(0.9) lower than 60 microns;
   microparticles (b) of said excipient have a mass median diameter (MMD) of between 2 and 15 microns;
   microparticles (a) of said active ingredient have a mass median diameter (MMD) of between 1 and 4 microns; and
   microparticles (a) of said active ingredient and microparticles (b) of said excipient are present in a weight ratio of between 1:9 and 1:90.

2. A powder formulation according to claim 1, wherein microparticles (a) of said active ingredient and microparticles (b) of said excipient are present in a weight ratio of between 1:15 and 1:80.

3. A powder formulation according to claim 2, wherein said microparticles (b) of said excipient have a MMD of between 2 and 10 µm.

4. A powder formulation according to claim 3, wherein said excipient is lactose.

5. A powder formulation according to claim 4, wherein said lactose is α-lactose monohydrate.

6. A powder formulation according to claim 2, wherein said microparticles (b) of said excipient have a MMD of between 3 and 7 µm.

7. A powder formulation according to claim 2, wherein said excipient is lactose.

8. A powder formulation according to claim 7, wherein said lactose is α-lactose monohydrate.

9. A powder formulation according to claim 1, wherein said microparticles (b) of said excipient have a MMD of between 2 and 10 µm.

10. A powder formulation according to claim 9, wherein said excipient is lactose.

11. A powder formulation according to claim 10, wherein said lactose is α-lactose monohydrate.

12. A powder formulation according to claim 9, wherein said microparticles (b) of said excipient have a MMD of between 3 and 7 µm.

13. A powder formulation according to claim 1, wherein said microparticles (b) of said excipient have a MMD of between 3 and 7 µm.

14. A powder formulation according to claim 1, wherein said excipient is lactose.

15. A powder formulation according to claim 14, wherein said lactose is α-lactose monohydrate.

16. A powder formulation according to claim 1, which further comprises one or more additives.

17. A powder formulation according to claim 16, which comprises at least one additive is selected from the group consisting of an anti-adherent, a water-soluble surface active material, and a water-insoluble lubricant.

18. A powder formulation according to claim 17, which comprises magnesium stearate.

19. A powder formulation according to claim 1, wherein said powder comprises additional carrier particles.

20. A powder formulation according to claim 19, wherein said additional carrier particles comprise fine particles having a MMD lower than 35 µm, coarse particles having a MMD higher than 90 µm, or a mixture thereof.

21. A powder formulation according to claim 20, wherein said additional carrier particles comprise:
   i) a fraction of fine particles comprising a mixture composed of carrier particles and particles of an additive;
   ii) a fraction of coarse carrier particles.

22. A powder formulation according to claim 21, wherein the fine and coarse carrier particles comprise at least one sugar selected from the group consisting of glucose, arabinose, maltose, saccharose, dextrose, and lactose.

23. A powder formulation according to claim 1, wherein said active ingredient is a long acting beta$_2$-agonist.

24. A powder formulation according to claim 1, further comprising a corticosteroid selected from the group consisting of budesonide, an epimer of budesonide, beclometasone dipropionate, mometasone furoate, flunisolide, ciclesonide, rofleponide, fluticasone propionate, and triamcinolone acetonide.

25. A powder formulation according to claim 1, further comprising an anticholinergic/antimuscarinic agent selected from the group consisting of ipratropium bromide, an enantiomer of ipratropium bromide, oxytropium bromide, an enantiomer of oxytropium bromide, tiotropium bromide, an enantiomer of tiotropium bromide, glycopyrrolate bromide, an enantiomer of glycopyrrolate bromide, revatropate, and an enantiomer of revatropate.

26. A powder formulation according to claim 1, further comprising a phosphodiesterase-4 (PDE-4) inhibitor.

27. A process for preparing a powder formulation according to claim 1, comprising:
    mixing said active ingredient and said excipient, to obtain a mixture; and
    micronizing said mixture by milling.

28. A process for preparing a powder formulation according to claim 1, comprising:
    micronizing said active ingredient, to obtain microparticles (a);
    micronizing said excipient, to obtain microparticles (b); and
    mixing said microparticles (a) and said microparticles (b).

* * * * *

UNITED STATES PATENT AND TRADEMARK OFFICE
CERTIFICATE OF CORRECTION

PATENT NO. : 8,153,104 B2
APPLICATION NO. : 10/592701
DATED : April 10, 2012
INVENTOR(S) : Roberto Bilzi et al.

It is certified that error appears in the above-identified patent and that said Letters Patent is hereby corrected as shown below:

On the title page, Item (75), the inventors information is incorrect. Item (75) should read:

-- (75) Inventors: Roberto Bilzi, Parma (IT); Angela Armanni, Parma (IT); Roberto Rastelli, Parma (IT); Daniela Cocconi, Parma (IT); Rossella Musa, Parma (IT) --

On the title page, Item (86), the Pct information is incorrect. Item (86) should read:

-- (86) PCT No.: PCT/EP2005/002789

§ 371 (c)(1),
(2), (4) Date: January 22, 2007 --

On the title page, Item (30), The Foreign Application Priority Data information is incorrect. Item (30) should read:

-- (30)    Foreign Application Priority Data

Mar. 17, 2004  (EP)...................04006430 --

Signed and Sealed this
Twenty-ninth Day of May, 2012

David J. Kappos
*Director of the United States Patent and Trademark Office*